(12) United States Patent
Schwarz

(10) Patent No.: US 12,035,883 B2
(45) Date of Patent: *Jul. 16, 2024

(54) ENDOSCOPE WITH CLEANABLE ROTARY DRUM

(71) Applicant: KARL STORZ SE & Co. KG, Tuttlingen (DE)

(72) Inventor: Peter Schwarz, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 333 days.

This patent is subject to a terminal disclaimer.

(21) Appl. No.: 17/456,700

(22) Filed: Nov. 29, 2021

(65) Prior Publication Data

US 2022/0175223 A1   Jun. 9, 2022

(30) Foreign Application Priority Data

Dec. 9, 2020   (DE) ..................... 10 2020 132 773.0

(51) Int. Cl.
*A61B 1/00* (2006.01)
*A61B 1/015* (2006.01)
*A61B 1/12* (2006.01)

(52) U.S. Cl.
CPC ...... *A61B 1/00096* (2013.01); *A61B 1/00091* (2013.01); *A61B 1/00183* (2013.01); *A61B 1/015* (2013.01); *A61B 1/126* (2013.01); *A61B 1/128* (2013.01)

(58) Field of Classification Search
CPC ............ A61B 1/00091; A61B 1/00183; A61B 1/051; A61B 1/0627; A61B 1/126; A61B 2017/1648

See application file for complete search history.

(56) References Cited

U.S. PATENT DOCUMENTS

| | | | | | |
|---|---|---|---|---|---|
| 3,145,249 | A | * | 8/1964 | Meltzer | G02B 23/26 15/250.1 |
| 3,924,608 | A | * | 12/1975 | Mitsui | A61B 1/00165 600/581 |
| 5,518,502 | A | * | 5/1996 | Kaplan | A61B 1/127 600/156 |
| 2003/0032863 | A1 | | 2/2003 | Kazakevich | |
| 2005/0234296 | A1 | * | 10/2005 | Saadat | A61B 1/0008 600/173 |
| 2009/0088631 | A1 | | 4/2009 | Dietz et al. | |
| 2013/0190562 | A1 | * | 7/2013 | Smith | A61B 1/0052 600/107 |

(Continued)

FOREIGN PATENT DOCUMENTS

| | | |
|---|---|---|
| DE | 100 24 728 A1 | 11/2001 |
| DE | 10 2005 015 522 A1 | 10/2006 |
| WO | 2021/013963 A1 | 1/2021 |

*Primary Examiner* — Aaron B Fairchild
*Assistant Examiner* — Stephen Floyd London
(74) *Attorney, Agent, or Firm* — Eversheds Sutherland (US) LLP

(57) ABSTRACT

An endoscope with a rotation drum or a rotation module and an elongated rigid and/or flexible shaft tube which, at a distal end, by means of a bearing fork, rotatably bears the rotation drum about a first axis of rotation, and wherein an optical imaging system is disposed within the rotation drum. The bearing fork here has at least one first fluid conduit and at least one nozzle in order to clean and/or to cool the imaging system.

10 Claims, 3 Drawing Sheets

(56) References Cited

U.S. PATENT DOCUMENTS

| | | | |
|---|---|---|---|
| 2013/0242071 A1* | 9/2013 | Wada | A61B 1/00183 |
| | | | 348/76 |
| 2014/0235944 A1* | 8/2014 | Feuer | A61B 1/126 |
| | | | 600/109 |
| 2014/0249369 A1* | 9/2014 | Hanabusa | A61B 1/051 |
| | | | 600/109 |
| 2015/0216402 A1* | 8/2015 | Ray | A61B 1/00096 |
| | | | 600/109 |
| 2015/0359420 A1 | 12/2015 | Hatase et al. | |
| 2017/0224197 A1 | 8/2017 | Green et al. | |
| 2019/0381290 A1* | 12/2019 | Saadat | A61M 29/00 |
| 2022/0248946 A1* | 8/2022 | O'Callaghan | A61B 1/00188 |

* cited by examiner

ENDOSCOPE WITH CLEANABLE ROTARY DRUM

TECHNICAL FIELD

The present invention relates to an endoscope with a cleanable rotation drum for medical uses according to the preamble of claim 1.

BACKGROUND OF THE INVENTION

WO 2017/040692 A1 discloses such an endoscope with a spherical rotation drum on an elongated rigid shaft tube, especially for use as a disposable instrument, which is rotatably mounted in a bearing fork at a distal end of the rigid shaft tube and can be rotated with a control conduit within the rigid shaft tube. The rotation drum has an imaging system within it and is connected by electronic elements within the rigid shaft tube, and it is possible at the same time to guide a liquid through the interior of the rigid shaft tube. The imaging system may be cleaned by pivoting the imaging system with a viewing direction, especially imaging optics of the viewing system, into the interior of the rigid shaft tube. In this pivoted cleaning position of the rotation drum, the imaging system can be flushed and cleaned by means of the liquid within the rigid shaft tube.

A shaft or typically a shaft tube of the endoscope may be rigid or flexible, or flexible in sections. Without any more specific description, the shaft tube hereinafter is understood to mean a rigid and/or flexible shaft tube.

In the cleaning position, the imaging system is thus facing away from the operation region to be observed, and tracking of an object in the operation region has to be stopped for the cleaning. This can result in unwanted stoppage and impairment of a medical, especially surgical, operation.

SUMMARY OF THE INVENTION

It is an object of the present invention to propose an endoscope which, avoiding the problems known from the prior art, enables cleaning during the use of the endoscope without alteration of the viewing direction, for example of an operation region, and simultaneously of improving temperature control, especially cooling, of the imaging system.

It is a further object to specify a method of cleaning the imaging system.

This object is achieved with regard to the endoscope by the features of independent claim 1 and with regard to the method by the features of claim 11.

Advantageous embodiments are the subject of the dependent claims.

According to the invention, an endoscope is proposed with a rotation drum or a rotation module and an elongated rigid and/or flexible shaft tube which, at a distal end, by means of a bearing fork, rotatably bears the rotation drum about a first axis of rotation, and wherein an optical imaging system is disposed within the rotation drum. The bearing fork here has at least one first fluid conduit and at least one nozzle in order to clean and/or to cool the imaging system.

In the context of the invention, the rotation drum or the rotation module is generally understood to mean a device for accommodating an imaging system, preferably a pivotable or rotatable device at a distal end of the shaft tube, and is therefore preferably referred to as rotation drum in the context of the invention, in a preferred form being a rotation module in the form of a drum.

The fluid in the context of the invention may preferably be understood to mean a liquid and/or gas, preferably with use of a sterile fluid for a medical use, such as processed oxygen as air/gas and a physiological saline solution as liquid.

Nozzles are understood to mean exit holes from the fluid channel through a wall of the bearing fork in order to spray the fluid onto the object to be cleaned at a higher speed than in the fluid conduit.

It has been recognized in the invention that, astonishingly, the use of the at least one first fluid conduit in the bearing fork allows nozzles to be disposed at a short distance from the rotation drum and likewise the imaging system. As a result, in a particularly effective manner, it is possible to rinse the rotation drum with a fluid in order to clean and/or to cool/adjust the temperature of the imaging system and/or to deflect an influx of contaminated fluid. Thus, it is not necessary to rinse an entire operation region with fluid; instead, it is possible even with a small use of fluid to locally clean the imaging system, especially also with a flow of air for use in a dry operation region. By virtue of the small distance and preferably the alignment of the at least one nozzle onto the imaging system, cleaning is possible in a particular viewing direction or a viewing region without, for example, having to pivot the rotation drum with the viewing direction in the direction of the interior of the shaft tube.

Cooling of the rotation drum is required particularly on account of evolution of heat in the operation of the electronic components of the imaging system with an electronic image sensor and/or lighting unit.

Alternatively, the fluid conduit may be used for control of the rotation drum temperature. For instance, as an alternative to cooling, it may also be necessary to preheat the imaging system prior to an operation to the expected ambient temperature in an operation region. Typically, a rise in the ambient temperature is to be expected, and preheating can prevent fogging of the imaging optics of the imaging system. Especially in order to prevent fogging of the imaging optics in a dry operation region, a flow of air or gas is sufficient as fluid.

It has also been recognized in the invention that the guiding of fluid within the bearing fork can also suck in fluid from the operation region. As a result, it is possible to suck in a fluid that could potentially contaminate the imaging system. For this case in particular, the nozzles may also be larger than the cross section of the fluid conduit in order preferably to reduce congestion/blocking of the nozzles by a contaminating fluid, for example by tissue residues.

In a preferred embodiment, the bearing fork, at a position of a field of view of the imaging system, protrudes at least partly in the viewing direction of the imaging system, preferably along a longitudinal axis of the shaft tube, with at least one first nozzle disposed at a distal end of the bearing fork in order preferably to clean the field of view of the imaging system with a fluid. In this way, in particular, the field of view of the imaging system can be cleaned directly, without rinsing, by means of a spray jet/fluid flow from the at least one first nozzle, in order thus also to improve the cleaning effect by mechanical washing-off. The bearing fork has preferably been prolonged in such a way as not to increase the external diameter of the distal end of the endoscope.

The projecting bearing fork also advantageously allows the rotation drum to be protected from damage.

In a particularly advantageous embodiment of the invention, the at least one first nozzle is aligned such that a fluid flow exits from the at least one first nozzle at an angle between 120° and 240°, preferably 180°, based on the longitudinal axis of the shaft tube. This allows an imaging system, particularly with a viewing direction of 0°, to be cleaned during the guiding of the endoscope into the operation region.

It is additionally preferable that at least one second nozzle is disposed in the region of a mounting position of the rotation drum and is directed toward the at least one side wall of the rotation drum. The at least one second nozzle is preferably provided in addition to the at least one first nozzle at the distal end of the bearing fork. This allows the flow to access an increased outside area of the rotation drum, and heat transfer to be improved, in order to adjust the temperature of the rotation drum, especially to cool the electronic components within the rotation drum. In addition, it is thus possible to rinse the region between the bearing fork and the side wall of the rotation drum that is difficult for a fluid flow to access and to prevent contamination and sticking of the rotation drum.

In one development, the at least one side wall of the rotation drum has preferably been provided with a coating having microstructures that increases the surface area of the at least one side wall. This can further improve the heat transfer from the side wall to a cooling fluid.

Further preferably, the fluid can be guided into the at least one first fluid conduit by means of at least one second fluid conduit within the shaft tube.

Preferably, the at least one second fluid conduit is part of a working channel which, in modular form, preferably has an air conduit and/or a liquid supply conduit and a liquid removal conduit. Especially since the imaging system with a supply conduit is not disposed within the shaft tube, it is especially possible to provide multiple channels, such as the air conduit together with the liquid supply conduit and the liquid removal conduit, within the shaft tube. There is advantageously no need for any kind of main shaft around the shaft tube or conduction of fluid that increases the external diameter of the shaft tube. The functionality of the at least one second fluid conduit may include the cleaning of the optics of a rotated rotation drum and/or cooling of the reverse side of the rotation drum and/or flushing and insufflation of a fluid into an operation region.

Advantageously, the air conduit is used in a dry operation region in order to dry the rotation drum after cleaning of the optics and/or to cool the rotation drum and the electronic components of the imaging system. The cleaning of the optics of the endoscope can also take place in a dry operation region in a cleaning position in which the rotation drum has especially been rotated in such a way that the field of view is directed onto the distal end of the shaft tube and the working channel. In this cleaning position, the imaging system can be rinsed with a rinse fluid from the liquid feed conduit, in which case the rinse liquid is removable by the liquid removal conduit and hence escape of rinse liquid into a dry operation region can be minimized. It is preferably possible with the air conduit to remove the rinse liquid from the imaging system in order to prevent distortion of the field of view of the imaging system by droplet formation. Further preferably, the liquid supply conduit and preferably also the air conduit may be designed as a spray nozzle in order to improve the cleaning action. For a watery or wet operation region or environment of the endoscope, the liquid feed conduit and the liquid removal conduit are preferably disposed in the working channel in order to rinse the reverse side of and control the temperature of the rotation drum, and to rinse the operation region. For the rinsing of the medical operation region, the shaft tube preferably has holes around its circumference at a distal end and/or a preferably slot-shaped opening of the working channel in order to connect the at least one second fluid conduit, preferably at least the liquid removal conduit, to the operation region. More particularly, the shaft tube is open beyond the rotation drum in order to assure free escape of the rinse fluid, especially the rinse water.

In a further embodiment, the bearing fork has a first limb and a second limb, and bears the rotation drum (20) pivotably therebetween, with at least one first fluid conduit and at least one nozzle formed in each of the limbs. In this way, the rotation drum is cleanable and temperature-controllable from the side and from two directions.

Preferably, at least one nozzle in a first limb of the bearing fork is connected to a fluid conduit as liquid conduit, especially water conduit, and at least one second nozzle in a second limb of the bearing fork with a fluid conduit as gas/air conduit. The liquid conduit can rinse soiling of the imaging system, especially the imaging optics. The gas/air conduit can prevent soiling by dust or fogging, particularly for a dry operation environment, preferably by sustained flow toward the imaging system.

In a preferred development, the bearing fork of the rotation drum has a rounded distal end. With this rounded end, the endoscope can be guided into an operation region with a low risk of injury.

According to the teaching of the invention, it may be the case that the rotation drum is pivotable about a first axis of rotation by means of at least one control conduit and the at least one control conduit of the rotation drum runs along an outside/outer face of the shaft tube, preferably without limiting a working channel within the shaft tube and the internal diameter of the shaft tube, and has been secured on the rotation drum at at least a lever margin from the at least one axis of rotation.

Preferably, the at least one control conduit can be wound up along at least one winding curve, preferably on the outer circumference of the rotation drum. This allows the control mechanics to be executed in a particularly simple manner, and there is no requirement for any maintenance-intensive or fault-prone gears or transmissions and the bearings thereof.

It is further preferable that the at least one control conduit of the rotation drum is executed as a supply conduit for the imaging system, preferably as a flexible circuit board or as a cable, for electronic circuits in the interior of the rotation drum. In this way, aside from the electrical or electronic actuation of the rotation drum, it is also possible to implement the mechanical control, especially pivoting by means of the control conduit.

The supply conduit may have electronic circuits, especially electronically adjustable imaging optics and/or an electronic image sensor or sensor of the imaging system and/or an illumination device, preferably comprising LEDs. The simultaneous use of the supply conduit as control conduit makes it possible, in a particularly advantageous manner, to dispense with a further control conduit for the rotation of the rotation drum.

Alternatively or additionally to the at least one second fluid conduit within the shaft tube, the at least one first fluid conduit may also be connected to a further external fluid conduit. This external fluid conduit is preferably run along the outside/outer surface of the shaft tube together with the at least one control conduit of the rotation drum. As a result, it is possible to use a working channel in the interior of the shaft tube for other functions.

This external fluid conduit may alternatively also be wound onto the rotation drum together with the at least one control conduit, which is designed to flush an operation region with a fluid.

More preferably, the at least one control conduit is run within a recess, preferably with a protective collar in the outer surface of the shaft tube, with the recess preferably running parallel to the longitudinal axis of the shaft tube. As a result, the at least one control conduit is run in a space-saving and form-fitting manner along the outside of the shaft tube in order firstly to protect the at least one control conduit from mechanical outside influences and in order secondly to prevent any risk of injury or trapping of tissue during an operation.

For the control of the rotation drum, resetting means, preferably a torsion spring at a bearing point of the rotation drum, are disposed on the rotation drum. The torsion spring here counteracts any mechanical torque on the at least one control conduit under tensile stress, in order to put a pivoted rotation drum into a starting position. The torsion spring thus preferably counteracts operation of the at least one control conduit in such a way that the at least one control conduit does not have to be subjected to a compression force for rotation of the rotation drum and in order to be able to use a flexible control conduit.

Alternatively or additionally, the rotation drum may be retractable by a further control conduit on the opposite side and/or be operable by means of a compression force with a dimensionally stable control conduit or a kind of Bowden cable or a kind of control rod or toothed rack.

Further in the alternative, the further control conduit may preferably take the form of a wire, in which case a resetting means, preferably a spring, especially a helical spring, is preferably secured in a handle for resetting of the rotation drum.

The working channel within the shaft tube is preferably designed to accommodate at least one instrument and/or includes at least one instrument in order to be able to conduct preferably medical operations in the operation region and especially in the field of view of the imaging system. This at least one instrument has a controllable tool at a distal end, for example a punching tool or cutting tool akin to a pair of scissors. The accommodation of the at least one instrument may be provided additionally or alternatively to the at least one second fluid conduit within the shaft tube. By virtue of the external control conduit and especially the external supply of the imaging system, the relatively large working channel can be used for at least one instrument and simultaneously a multitude of second fluid conduits.

In one development, the shaft tube is open in an upper section, in which case the at least one control conduit is run along an opposite lower section in order preferably to displace/bend a flexible instrument in a direction at right angles to the longitudinal axis of the shaft tube and into the open upper section. In this way, the instrument, especially the functional parts and tools at the distal end of the at least one instrument, may be moved out of the shaft tube into an operation region and, at the same time, the operation region can be monitored with the imaging system within the rotation drum.

In a further embodiment, the bearing fork is rotatable about a second axis of rotation, in which case the at least one nozzle is preferably connected by means of a flexible tube connection to the at least one second fluid conduit and/or an external further fluid conduit along the shaft tube.

Particularly for the use of the endoscope with at least one instrument, it is preferably the case that the bearing fork is secured to the shaft tube so as to be pivotable about a second axis of rotation and the working channel, in a pivoted state of the bearing fork, is open along the longitudinal axis in order especially to guide an instrument from the working channel into the operation region, with the bearing fork preferably being controllable by a further control conduit. The further control conduit is preferably likewise run along the outside of the shaft tube in order not to restrict the working channel in the interior of the shaft tube. By this embodiment, in particular, a rigid instrument can be guided parallel to the longitudinal axis of the shaft tube into the operation region. In addition, by means of a rotation of the rotation drum about a second axis of rotation, a preferably flexible instrument is bendable in a direction at right angles to the longitudinal axis of the shaft tube. As well as the guiding of the at least one instrument, the pivotable bearing fork advantageously enables an extended field of view of the imaging system, including, for example, behind barriers or corners or a view along the outside of the shaft tube. For example, the function of the guiding of the at least one control conduit along the shaft tube can also be verified by means of the imaging system. In addition, the open working channel can promote purging or suction of a fluid from an operation region.

Alternatively or additionally, the bearing fork may also be connected to the shaft tube by means of a flexible or elastically deformable element, in which case the flexible element forms a passive reset force in order to pivot the bearing fork about the second axis of rotation and open the working channel for the instrument.

The external diameter of the shaft tube is preferably 3 mm to 6 mm, and the rotation drum preferably does not exceed this external diameter. Such shaft tubes are suitable for a multitude of non-invasive medical operations.

In a further-preferred embodiment, multiple control conduits can be wound around the circumference of the rotation drum in different winding curves, especially with a different distance from the axis of rotation, in order to perform different rotary displacement of the rotation drum for the same displacement distance of the control conduit. More particularly, the displacement distance parallel to the longitudinal axis of the shaft tube and the different rotary displacement can lead to predefined viewing angles of the imaging system or to different rotation speeds; for the same displacement distance of the control conduit, the rotary displacement of the rotation drum decreases with decreasing distance from the first axis of rotation of the rotation drum. The tensile force needed for the rotary displacement may also be adjusted via the different distances.

More preferably, the different winding curves are arranged stepwise along the first axis of rotation on the circumference of the rotation drum; the winding curves are preferably arranged with decreasing distance from the first axis of rotation in the direction of the outer faces of the rotation drum.

The invention also relates to a method of cleaning an imaging system, preferably an above-described endoscope with rotation drum, wherein the rotation drum is first pivoted in a viewing direction, preferably in a direction facing away from the shaft tube, in order to examine an operation region for example, and then is contacted in a sustained manner or at least intermittently with a fluid stream from at least one first fluid conduit having at least one nozzle within a bearing fork of the rotation drum. This allows the imaging system to be cleaned without interrupting or affecting an operation procedure.

Further advantages and details of the invention will be apparent from the description of preferred embodiments of the invention that follows, and from merely schematic drawings.

BRIEF DESCRIPTION OF THE DRAWINGS

The figures show.

Identical elements or elements with the same function are given the same reference numerals in the figures.

DETAILED DESCRIPTION

Figure 1A:
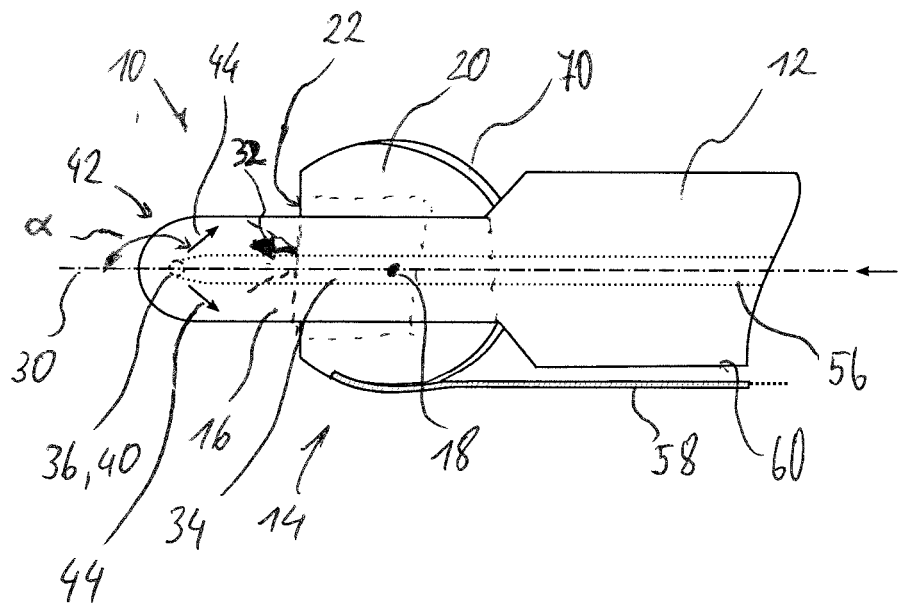
FIG. 1a: a side view of a distal end of an endoscope with rotation drum and bearing fork with fluid conduit.

FIG. 1a shows an endoscope 10 with a rotation drum 20 at a distal end 14 of an elongated rigid shaft tube 12, with the rotation drum 20 borne by means of a bearing fork 16 at the distal end 14 of the shaft tube so as to be rotatable about a first axis of rotation 18.

Figure 1B:
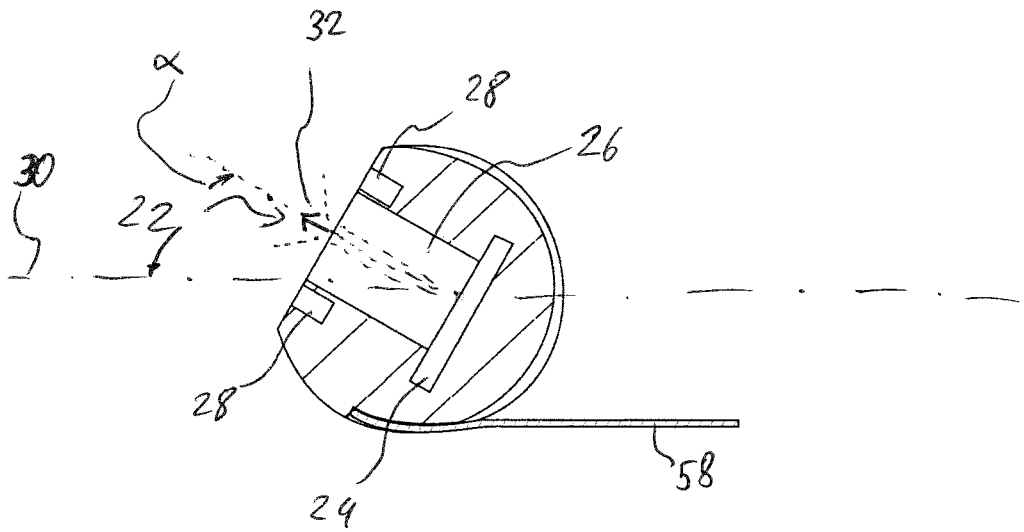
FIG. 1b: a longitudinal view of the rotation drum according to FIG. 1a,
FIG. 2a: a side view of the endoscope according to FIG. 1a with first and second nozzles in the bearing fork.

As shown in detail in FIG. 1b, an optical imaging system 22 mounted within the rotation drum 20 preferably comprises an electronic image sensor 24, imaging optics 26 and an illumination device 28.

A viewing direction 32 of the imaging system 22 is pivotable by an angle α relative to the longitudinal axis 30 of the shaft tube 12, without restriction of the viewing direction 32 of the imaging optics 26 by the bearing fork 16. By pivoting the rotation drum 20 and hence the viewing direction 32, it is possible to cover an angle α of preferably more than 130°. By rotating the shaft tube 12 about the axis of rotation 30, it is possible to extend the observation region of the imaging system 22.

Figure 2A:
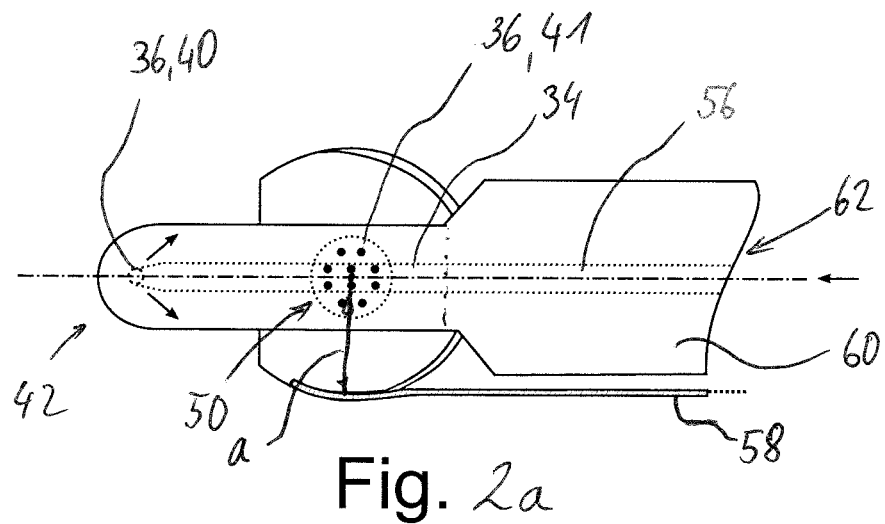
FIG. 2b: a top view of the endoscope according to FIG. 2a along a longitudinal axis.

As shown in FIG. 1a and FIG. 2a, the bearing fork 16 has at least one first fluid conduit 34 and at least one nozzle 36 in order to clean and/or to cool the imaging system 22.

The bearing fork 16 is preferably extended along the longitudinal axis 30 of the shaft tube 18 to a position of the field of view 38 of the imaging system 22. As shown in FIG. 1a, at least one first nozzle 36, 40 is mounted at a distal end 42 of the bearing fork in order to clean the field of view 38 of the imaging system 22 with a fluid flow 44. In the case of extension of the bearing fork 16 along the longitudinal axis 30, the field of view 38 is cleanable at a viewing angle 32 having an angle α of 0°. More preferably, in this position, the endoscope 10 can be guided to an operation region, in which case the field of view 38 is simultaneously cleanable with the at least one first nozzle 36, 40.

The at least one first nozzle 26 is preferably aligned such that the fluid flow 44 exits from the at least one first nozzle 36, 40 at an angle α between 120° and 240°, preferably 180°, based on the longitudinal axis 30 of the shaft tube 12. In this way, the field of view 38 of the imaging system 22 is cleanable over a large area even in the case of a small distance from the at least one first nozzle 36, 40. More particularly, in the case of a small distance, the cleaning can be improved by pivoting of the rotation drum 20.

Alternatively, the fluid flow 44 shown in FIG. 1 can also be reversed in order to suck in a fluid or a potentially contaminating medium in front of the field of view 38 and in order thus to prevent contamination of the field of view 38.

Figure 2B:
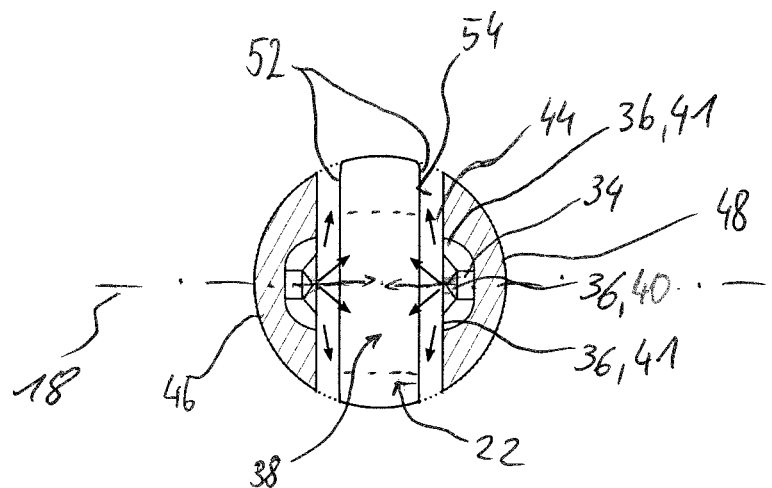

As shown in FIG. 2a, preferably at least one second nozzle 36, 41, preferably a multitude of second nozzles 36, 41, is disposed in the region of a bearing position 50 of the rotation drum 20. The at least one second nozzle 36, 41, according to FIG. 2b, is directed toward the at least one side wall 52 of the rotation drum 20 in order to control its temperature, especially in order to cool it. What is shown here in FIG. 2b is the fluid flow 44 onto the at least one side wall 52 of the rotation drum 20 and onto the field of view 38 of the imaging system 22. The fluid from the at least one second nozzle 36, 41 may be a gas and/or a liquid; a liquid improves heat transfer and a gas is preferably usable in a dry operation region.

More preferably, the at least one side wall 52 of the rotation drum has been provided with a coating having microstructures (not shown) that increases the surface area of the at least one side wall 52, in order to further improve heat transfer.

Preferably, according to FIG. 1a or FIG. 2a, a fluid can be guided into the at least one first fluid conduit 34 by means of an at least one second fluid conduit 56 within the shaft tube 12. The at least one second fluid conduit 56 here is preferably disposed in a working channel 62 of the shaft tube 12.

The bearing fork 16 preferably has a first limb and a second limb 46, 48, according to FIG. 2b, in order to bear the rotation drum 20 pivotably therebetween, with at least one first fluid conduit 34 and at least one nozzle 36 formed in each of the limbs 46, 48.

Preferably, as shown in FIG. 2a, the at least one first nozzle 36, 40 and the at least one second nozzle 36, 41 are connected to a common first fluid conduit 34. Alternatively, a multitude of first fluid conduits 34 may also be provided in order, for example, to supply the at least one first nozzle 36, 40 and the at least one second nozzle 36, 41 with different fluids. For instance, it is preferably possible to fill the at least one first nozzle 36, 41 with a liquid in order to improve heat transfer and temperature control of the rotation drum 20. It is preferably possible here to fill the at least one first nozzle 36, 40 with a gas or air in order to clean the field of view 38 of the imaging system 22. A multitude of further combinations is possible here, which especially depends on an environmental condition in an operation region. For example, exclusively a gas or flow of air may be preferable for a dry operation region, and exclusively a flow of liquid for a wet operation region.

In addition, the variation of first fluid conduits 34 may also be based on the two limbs 46, 48. For instance, at least one nozzle 36 in a first limb 46 of the bearing fork 16 may be connected to a liquid conduit, especially water conduit, and at least one nozzle 36 in a second limb 48 to a gas/air conduit.

More preferably, the bearing fork 16 of the rotation drum 20, according to FIG. 1a or FIG. 1b, has a rounded distal end 42.

As shown in FIG. 1a or FIG. 2a, the rotation drum 20 is preferably pivotable about a first axis of rotation 18 by means of a control conduit 58, with the control conduit 58 running along an outside/outer face 60 of the shaft tube 12, preferably without limiting the working channel 62 within the shaft tube 12 and an internal diameter of the shaft tube 12. The control conduit 58 has been secured on the rotation drum 20 at at least a lever margin a from the at least one axis of rotation 18. The rotation drum 20, by a movement of the control conduit 58, is preferably rotatable parallel to the longitudinal axis of the shaft tube 12.

The rotation drum 20, according to FIG. 1a and FIG. 1b, is preferably in spherical or cylindrical form, with the rotation drum 20 preferably flattened at right angles to the viewing direction 32 of the imaging system 22 in order to accommodate the imaging optics 26 and the illumination device 28, preferably in the form of two LEDs, in a flattened region.

As shown in FIG. 1b, the control conduit 58 is preferably windable on a winding curve 70 along the outer circumference of the rotation drum 20. More preferably, the control conduit 58 is windable in such a way that the rotation drum 20, from a viewing angle 32 along the longitudinal axis 30 of the shaft tube, is windable by at least an angle α of 0° to 180° and hence the viewing angle 32 can be directed into the interior of the shaft tube 12 and a working channel 62. For the pivoting of the rotation drum 20, the control conduit 58 is designed to be at least partly flexible in order to wind it along the winding curve 70 of the rotation drum 20. The winding curve 70 along the outer circumference here may preferably be circular or oval-shaped.

Figure 3A:
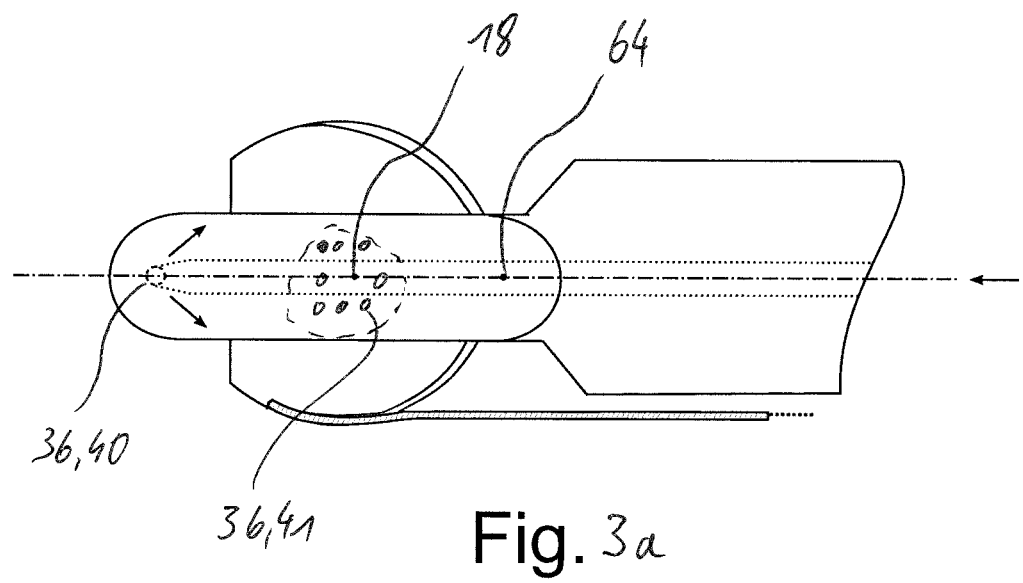
FIG. 3a: a side view of the endoscope according to FIG. 1a with rotatably mounted bearing fork.
Figure 3B:
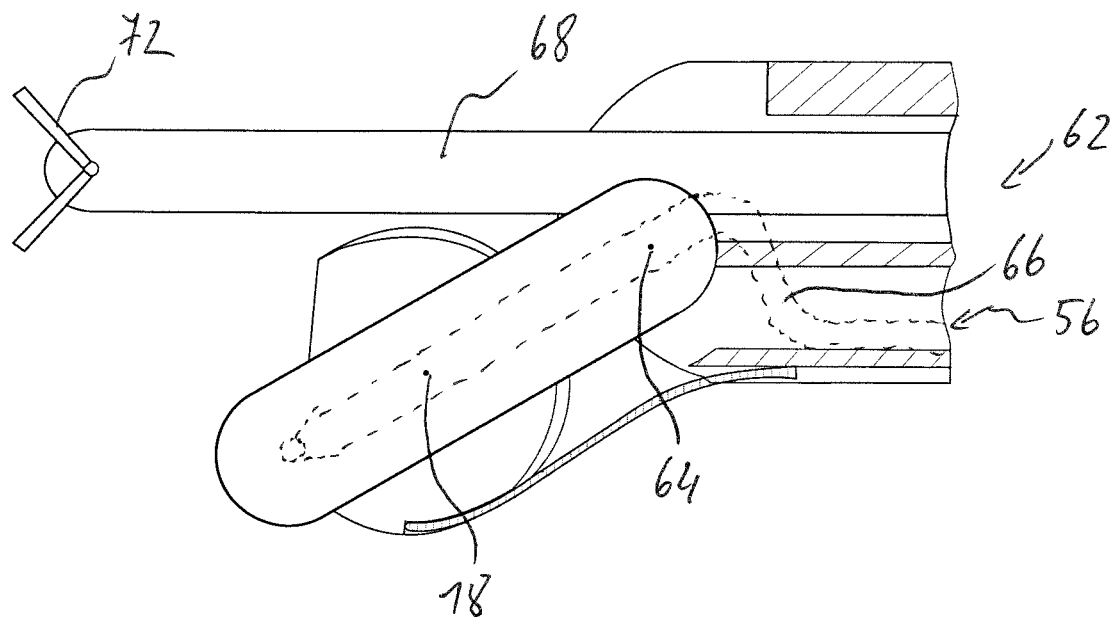
FIG. 3b: a side view of the endoscope according to FIG. 3a with an instrument and pivoted bearing fork.

As shown in FIG. 3a and FIG. 3b, the bearing fork 16, in one development, is rotatable about a second axis of rotation 64, with the at least one nozzle 36 preferably connected by means of a flexible tube connection 66 to the at least one second fluid conduit 56 and or an external further fluid conduit along the shaft tube 12.

Preferably with this rotatable bearing fork 16 about a second axis of rotation 64, as shown in FIG. 3b, the working channel 62 may be designed to accommodate and/or to include an instrument 68. This instrument 68 may have, at a distal end, a tool 72, for example a cutting tool or punching tool, adapted to the respective medical operation.

In a pivoted state of the bearing fork, according to FIG. 3b, the working channel 62 along the longitudinal axis 30 is open in such a way that a rigid instrument 68 can preferably be guided from the working channel 62 into the operation region. The bearing fork 16 is preferably controllable with a further control conduit (not shown) or another operating mechanism. Preferably an operating mechanism for flexible shaft tubes known, for example, from US 2015/0359420 A1.

The pivoting of the bearing fork 16 can likewise extend the field of view 38 of the rotation drum 20, in order, for example, also to be able to cover a field of view 38 of the imaging system 22 covered by the shaft tube 12 itself or to look beyond corners or barriers.

The invention also relates to a method of cleaning the imaging system 22 with rotation drum 20, wherein the rotation drum 20 is pivoted in a viewing direction 32, according to FIG. 1a, preferably at an angle α of 0°, in order to examine an operation region for example. Subsequently, the imaging system is contacted in a sustained manner or at least intermittently with a fluid stream 44 from at least one first fluid conduit 34 having at least one nozzle 36 within a bearing fork 16 of the rotation drum 20, preferably from the at least one first nozzle 36, 40.

The endoscope 10 described in this respect may be altered or modified in various ways without departing from the concept of the invention. For example, it is conceivable that the part of the bearing fork 16 that has been extended to the position of the imaging system 22 is bodily rotatable with the rotation drum in order to clean the imaging system irrespective of the pivoted position of the rotation drum 20.

In addition, it is conceivable to couple the cleaning and/or temperature control of the rotation drum 20 or of the imaging system 22 to a closed-loop control circuit, or to perform it in an automated manner, in order, for example, to establish a particular temperature or to clean the imaging system 22 as soon as soiling is detected, preferably by the image sensor 24.

LIST OF REFERENCE NUMERALS 10 endoscope
12 shaft tube
14 distal end of the shaft tube
16 bearing fork
18 first axis of rotation
20 rotation drum
22 imaging system
24 electronic image sensor
26 imaging optics
28 illumination device
30 longitudinal axis of the shaft tube
32 viewing direction of the imaging optics
34 first fluid conduit
36 nozzle
38 field of view of the imaging system
40 first nozzle
41 second nozzle
42 distal end of the bearing fork
44 fluid flow
46 first limb of the bearing fork
48 second limb of the bearing fork
50 bearing position of the rotation drum
52 side wall of the rotation drum
54 surface of the side wall
56 second fluid conduit
58 control conduit of the rotation drum
60 outside of the shaft tube
62 working channel
64 second axis of rotation
66 flexible tube connection
68 instrument
70 winding curve
72 tool
a lever margin
α angle between the viewing direction and the longitudinal axis

I claim:

1. An endoscope with a rotation drum and an elongated rigid and/or flexible shaft tube which, at a distal end, by means of a bearing fork, rotatably bears the rotation drum about a first axis of rotation, and wherein an optical imaging system is disposed within the rotation drum,
   wherein the bearing fork has at least one first fluid conduit and at least one first nozzle in order to clean and/or to cool the imaging system, and
   wherein the bearing fork has a first limb and a second limb, and bears the rotation drum pivotably therebetween, with the at least one first fluid conduit and the at least one first nozzle formed in each of the limbs.

2. The endoscope as claimed in claim 1,
   wherein the bearing fork, at a position of a field of view of the imaging system, protrudes at least partly in a viewing direction of the imaging system, with the at least one first nozzle disposed at a distal end of the bearing fork in order to clean the field of view of the imaging system with a fluid.

3. The endoscope as claimed in claim 2,
wherein the at least one first nozzle is aligned such that a fluid flow exits from the at least one first nozzle at an angle (α) between 120° and 240° based on a longitudinal axis of the shaft tube.

4. The endoscope as claimed in claim 1,
wherein at least one second nozzle is disposed in a region of a bearing position of the rotation drum and is directed toward at least one side wall of the rotation drum.

5. The endoscope as claimed in claim 1,
wherein at least one side wall of the rotation drum has been provided with a coating having microstructures that increases a surface area of the at least one side wall.

6. The endoscope as claimed in claim 1,
wherein a fluid is guided into the at least one first fluid conduit by means of an at least one second fluid conduit within the shaft tube.

7. The endoscope as claimed in claim 1,
wherein the bearing fork of the rotation drum has a rounded distal end.

8. The endoscope as claimed in claim 1,
wherein the rotation drum is pivotable about a first axis of rotation by means of at least one control conduit and the at least one control conduit of the rotation drum runs along an outside/outer face of the shaft tube, and has been secured on the rotation drum at at least a lever margin (a) from at least one axis of rotation.

9. The endoscope as claimed in claim 1,
wherein the bearing fork is mounted so as to be rotatable about a second axis of rotation,
wherein the at least one nozzle is connected, to at least one second fluid conduit and/or an external further fluid conduit along the shaft tube.

10. A method of cleaning an imaging system of an endoscope with rotation drum, as claimed in claim 1, wherein the rotation drum is pivoted in a viewing direction, in order to examine an operation region, and then is contacted in a sustained manner or at least intermittently with a fluid stream from at least one first fluid conduit having at least one nozzle within a bearing fork of the rotation drum.

* * * * *